United States Patent
Couderc et al.

(10) Patent No.: US 12,313,516 B1
(45) Date of Patent: May 27, 2025

(54) DEVICE FOR SPREADING OR COLOURING AND DETERMINING A SEDIMENTATION RATE

(71) Applicant: HORIBA ABX SAS, Montpellier (FR)

(72) Inventors: Guilhem Couderc, Montpellier (FR); Florent Beauducel, Montpellier (FR); Coralie Thoraval, Montpellier (FR)

(73) Assignee: HORIBA ABX SAS, Montpellier (FR)

( * ) Notice: Subject to any disclaimer, the term of this patent is extended or adjusted under 35 U.S.C. 154(b) by 0 days.

(21) Appl. No.: 18/856,813

(22) PCT Filed: Apr. 13, 2023

(86) PCT No.: PCT/FR2023/050536
§ 371 (c)(1),
(2) Date: Jan. 7, 2025

(87) PCT Pub. No.: WO2023/199001
PCT Pub. Date: Oct. 19, 2023

(30) Foreign Application Priority Data

Apr. 15, 2022 (FR) ........................... 2203573

(51) Int. Cl.
*G01N 15/05* (2006.01)
*G01N 1/28* (2006.01)
*G01N 33/49* (2006.01)

(52) U.S. Cl.
CPC ........... *G01N 15/05* (2013.01); *G01N 1/2813* (2013.01); *G01N 33/491* (2013.01); *G01N 2015/055* (2013.01)

(58) Field of Classification Search
CPC ..... G01N 2015/0073; G01N 2015/008; G01N 2015/055; G01N 2015/06; G01N 1/28;
(Continued)

(56) References Cited

U.S. PATENT DOCUMENTS

| | | | | |
|---|---|---|---|---|
| 4,848,900 A | * | 7/1989 | Kuo ....................... | G01N 15/05 73/61.64 |
| 5,745,227 A | * | 4/1998 | Dufresne ............... | G01N 15/05 436/70 |

(Continued)

FOREIGN PATENT DOCUMENTS

| | | |
|---|---|---|
| EP | 2921862 A1 | 9/2015 |
| IT | 20163693 A1 | 11/2017 |

(Continued)

OTHER PUBLICATIONS

International Patent Application No. PCT/FR2023/050536 filed Apr. 13, 2023; International Search Report / Written Opinion issued Jun. 28, 2023; 15 pages, English language translation included.

*Primary Examiner* — Hoa Q Pham
(74) *Attorney, Agent, or Firm* — Mueting Raasch Group

(57) ABSTRACT

A device for spreading or colouring and for determining a sedimentation rate includes a first group arranged so as to sample a blood sample from a tube and to carry out a smear test on the sample and a second group arranged so as to sample a blood sample from a tube and to carry out a sedimentation rate determination. At least one sampling member is controllable for an operation by the first group and an operation by the second group for sampling a blood sample so that a sample sampled for one group is not used by the other group. The second group is provided with a sensor. A converter is arranged so as to receive one or more light-transmission measurements from the sensor and to determine a sedimentation rate.

12 Claims, 4 Drawing Sheets

(58) Field of Classification Search
CPC ........ G01N 1/30; G01N 1/2813; G01N 1/272; G01N 15/05; G01N 21/27; G01N 33/48792; G01N 33/49; G01N 33/48707; G01N 35/10; G01N 27/3275
USPC .................. 356/39–41, 246; 436/70; 422/73, 422/560–561, 102, 58, 61; 73/61.65
See application file for complete search history.

(56) References Cited

U.S. PATENT DOCUMENTS

| | | | |
|---|---|---|---|
| 10,539,491 B2* | 1/2020 | Yang | G01N 33/49 |
| 2018/0313738 A1* | 11/2018 | Kawano | G01N 15/0227 |
| 2024/0159640 A1* | 5/2024 | Zheng | G01N 15/05 |

FOREIGN PATENT DOCUMENTS

| | | | |
|---|---|---|---|
| KR | 20160132638 A | * | 11/2016 |
| WO | WO 2021097610 A1 | | 5/2021 |

\* cited by examiner

DEVICE FOR SPREADING OR COLOURING AND DETERMINING A SEDIMENTATION RATE

This application is the § 371 U.S. National Stage International Application No. PCT/FR2023/050536, filed Apr. 13, 2023, which was published on Oct. 19, 2023, as International Publication No. WO2023199001A1 and claims priority to French Patent Application No. FR2203573, filed Apr. 15, 2022, the disclosures of which are incorporated by reference herein in their entireties.

The invention relates to the field of haematology, and more particularly to the determination of the sedimentation rate (hereinafter ESR, also so-called "erythrocyte sedimentation rate")

The sedimentation rate is part of the routine examinations with the complete blood count (hereinafter CBC standing for "Complete Blood Count") performed during a blood assessment and allows detecting the presence of inflammatory or infectious pathologies. For example, rheumatism, a cancer and other conditions leading to changes in protein concentration in blood. A high ESR indicates an inflammatory state without prejudging its nature. However, it happens that the ESR remains low while there is an inflammatory syndrome. Hence, a high ESR generally indicates the presence of a pathology. The association of this non-specific test with complementary examinations allows having a more accurate diagnosis.

The reference method for measuring the ESR is the Westergren method. A narrow tube with standardised dimensions is filled with a blood sample sampled with an anticoagulant, for example EDTA, and diluted with sodium citrate and placed vertically. The ESR measurement is the height, in millimetres, of the plasma column after one hour of sedimentation. For example, it is considered that a height smaller than 10 mm after the first hour of sedimentation is a normal value for a male adult. The limit of normality is not an absolute value but depends on the age and gender of the patient.

The ESR is the resultant of three steps: aggregation of the haematids or blood cells, sedimentation, and settling of the rolls.

The phenomenon of aggregation of the haematids is produced in particular by blood proteins with a force which is even greater as the concentrations of these are high. The formation of the aggregates is the stacking of the haematids into "rolls", and then in three-dimensional structures. The sedimentation rate depends on the dimensions of the aggregates and on the viscosity of the plasma.

During the last steps, the aggregates will sediment, i.e. they will progressively fall at the bottom of the tube, then compact, which will have the effect of separating the sample into a clear translucent portion (plasma), at the top, and a much darker portion (haematids) at the bottom. The ESR is measured by the height of the translucent portion.

The most relevant inflammatory parameter is the aggregation phenomenon which directly depends on the concentrations of the plasma proteins. It is this phenomenon which is measured by the present invention to return an ESR value. It is also a parameter that is non-specific, but which suppresses the interferences resulting from the last two steps of the ESR. There is no standardised parameter allowing expressing this aggregation rate or dynamics/kinetics. Hence, it is relevant to transpose aggregation measurement quantities into ESR.

Because of the amount of blood (1.6 ml) and the duration required for completion thereof (1 hour), the Westergren method is not compatible with haematology machines for CBC analysis. To overcome these problems, researches have been conducted in order to use extinction optical measurements (absorption and scattering) to determine the sedimentation rate, like in patent U.S. Pat. No. 6,632,679.

Some patents, as described in EP 2 921 862, have proposed integrating a modified ESR measurement in a blood test apparatus which samples an amount of blood and separates it into two portions which respectively undergo a count (CBC) and a sedimentation rate measurement.

Hence, this apparatus relates the count measurement and the sedimentation rate measurement, which is disadvantageous because it requires complex apparatuses to dispense via one single sample, two blood sample portions towards the counting section on one side and towards the sedimentation rate measuring section on another side, all the more so as the CBC and ESR measurement operations do not have the same needs in terms of preparation of the sample.

More generally, in automated laboratories of the TLA ("Total Laboratory Automation") type, the tube flow is managed in a fully automatic manner, from the most frequent tests to least frequent ones. The equipment required to feed the measurement cell with samples is by far the most expensive and complex portion, and comprises:

the interconnection to a chain,
the management of racks,
the stirring of the tubes,
the management of the tubes,
the sampling and transfer in the measurement cell,
the rinsing of the sampling device, and
the devices for controlling and transmitting the results.

Also, this results in a very high ratio (higher than 100) between the cost of the measurement system and that of the infrastructure required for managing the sample. In comparison, this ratio is much lower (2 to 5) for a CBC/DIF/RET measurement system or an automated spreading or colouring system commonly used in a haematology laboratory.

On the other hand, laboratories treating a large number of tubes on a daily basis require that the processing time of the newly arrived tubes is limited ("Turnaround time" or TAT) and this directly imposes the sizing of the CBC/DIF/RET measurement systems, and therefore their hardware cost.

On the other hand, since a small proportion of the treated tubes requires spreading or colouring (only 5 to 20%), this system is commonly oversized by all manufacturers.

Document WO 2021/097610 A1 describes a sample analyser comprising a module for measuring the erythrocyte sedimentation rate, a module for measuring the haemogram and a sample assignment module. The sample assignment module is used to collect a blood sample, assign a first portion of the blood sample to the erythrocyte sedimentation rate measurement module, and assign a second portion of the blood sample to the complete blood count measurement module. The erythrocyte sedimentation rate measurement module comprises a measurement tube and an optical measurement apparatus.

No known device allows carrying out an effective determination of the sedimentation rate measurement in a rapid and integrated manner in the context of the requirements of a modern laboratory.

The invention improves the situation. To this end, it provides a device for spreading or colouring and determining a sedimentation rate which comprises a first group arranged so as to sample a blood sample from a tube and to carry out a smear test on this sample, and a second group arranged so as to sample a blood sample from a tube and to carry out a sedimentation rate determination. The device comprises at least one sampling member which could be controlled for an operation by the first group and an operation by the second group for sampling a blood sample so that a sample sampled for the first group is not used by the second group, and that a sample sampled for the second group is not used by the first group, the second group being provided with a sensor comprising an infrared light source and an optical sensor arranged substantially opposite one another around a tube connected to an output end of the at least one sampling member so that the light emitted by the infrared light source reaches the optical sensor after having crossed said tube. The second group is further arranged so as to carry out a rinsing of the sampling member and of the tube between two sedimentation rate measurement determinations and the optical sensor is arranged so as to carry out a blank measurement after a rinsing operation. The device further comprises a converter arranged so as to receive a blank measurement and one or more light transmission measurement(s) from the optical sensor and to determine a sedimentation rate from the ratio between the blank measurement and the light transmission measurement(s).

This device is particularly advantageous because it allows carrying out the sedimentation rate measurement independently of the complete blood count. Thus, the sedimentation rate measurement, which remains a less systematic test, does not interfere with the architecture of the device in a manner likely to affect the other functionalities.

According to various embodiments, the invention may have one or more of the following features:
- the infrared light source and the optical sensor are arranged at a distance from the sampling end of the sampling member shorter than 10 cm,
- the second group is arranged at an inlet of the device upstream of the first group, or at the outlet of the device for carrying out spreading or colouring type complementary measurements downstream of the first group,
- the converter is arranged so as to determine a time point of measurement of the lowest light transmission, and a time point of measurement of the final light transmission,
- the optical sensor is arranged so as to implement a maximum gain between the time point of measurement of the lowest light transmission and the time point of measurement of the final light transmission, and to implement a minimum gain the rest of the time,
- the converter is arranged so as to calculate the sedimentation rate from the ratio between on the one hand the ratio between the blank measurement and the measurement at the time point of measurement of the final light transmission and, on the other hand, the ratio between the blank measurement and the measurement at the time point of measurement of the lowest light transmission,
- the optical sensor is controlled with a low gain before blood passes through the substantially transparent portion, and with a high gain afterwards, and
- the sampling member is a needle which could be controlled for sampling of a blood sample to which a tube is connected in which the substantially transparent portion is formed.

The invention also relates to a method for spreading or colouring and determining a sedimentation rate characterised in that it comprises using a device according to the invention, and in that carrying out a spreading or colouring on the one hand and determining a sedimentation rate on the other hand comprise sampling two distinct samples.

Other features and advantages of the invention will appear better upon reading the following description, with reference to examples given for illustrative and non-limiting purposes, with reference to the drawings wherein.

The drawings and the description hereinafter essentially contain elements of certain nature. Hence, they could not only serve to better understand the present invention, but also contribute to the definition thereof, where appropriate.

Figure 1:
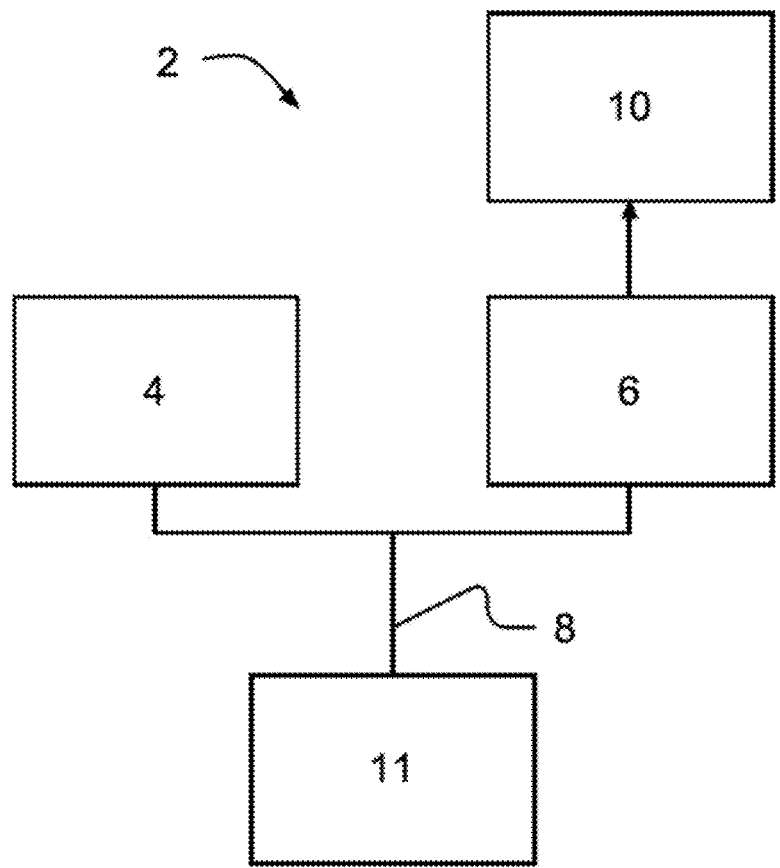
FIG. 1 shows a general schematic view of a device according to the invention.

FIG. 1 shows a general schematic view of a device 2 for performing a complete blood count and for determining the sedimentation rate measurement according to the invention. The device 2 comprises a first group 4, a second group 6, a sampling member 8 and a converter 10.

The first group 4 is arranged so as to carry out a blood smear test. Devices carrying out blood smear tests automatically are very commonly implemented in laboratories having to treat a large number of tubes on a daily basis. They are generally too oversized in terms of processing rate with regards to the needs of the laboratory.

This oversizing is directly related to the technical complexity of the different steps necessary for the preparation of the slide of each of the devices (sampling, deposition of a drop of aliquot over a glass slide, spreading, identification of the slide, vital colourations, etc.): the high rate is the only means available to manufacturers to optimise the marginal costs.

Since blood smear tests are less systematic tests than CBC, the Applicant has discovered that it was interesting to pool the resources of the first group 4 in order to add a determination of the measurement of the ESR by means of the group 6.

The second group 6 is arranged so as to determine an ESR measurement. It is this second group which is the main object of the invention. Indeed, as described in the introduction, this test, whether it is carried out according to the conventional method or by measuring the change in the light absorbance, is either tedious, or coupled to a CBC measurement, which slows down the entire device.

The implementation of the second group 6 according to the invention allows extrapolating a sedimentation rate measurement by changing the light absorbance in a manner decoupled from any CBC measurement or other blood measurements. For this purpose, the second group 6 is arranged so as to control the sampling member 8 which is herein a needle independently of the first group 4, i.e. the samples sampled by the first group 4 are used just to carry out a blood smear test, and the samples sampled by the second group 6 are used only for an ESR measurement.

Thus, as shown in FIG. 1, the first group 4 or the second group 6 controls the needle 8 to sample a blood sample in a blood tube 11. Afterwards, this sample is brought to the first group 4 to carry out a blood smear test, or to the second group 6 to carry out a measurement of the change in light absorbance. In the last case, the measurement is transmitted to the converter 10 which returns an ESR signal and/or an ESR measurement value.

Figure 2:
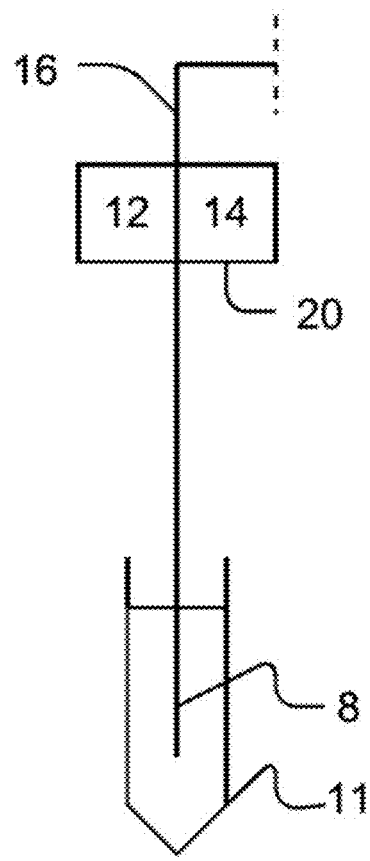
FIG. 2 shows a detail of making of an element of FIG. 1.

FIG. 2 shows an embodiment of the second measuring group 6. According to this example, the second measuring group 6 is made by means of an optical source 12 and an optical sensor 14 which are assembled opposite one another around a tube 16 which is intended to transport the blood sample sampled by the needle 8 from a blood tube 11 towards the inside of the device 2.

In the example described herein, the light source 12 is of the LED type with an infrared wavelength preferably in the range 700-980 nm and in particular 800 nm, which is an isosbestic point between oxyhaemoglobin and deoxyhaemoglobin, which makes the measurement insensitive to the blood oxygen saturation level. In the example described herein, the optical sensor 14 is of the photodiode type and may be selected from among PMT, PDA, CMOS, etc., sensors. In the example described herein, the tube 16 is made of Teflon and is connected to the needle 8. Alternatively, the tube 16 may be made of glass or plastic and should be selected so as to offer a good transparency to the wavelength of the light source 12.

The light source assembly 12 and optical sensor 14 could be seen as one single sensor 20 of the second group 6. Like in the example described herein, it may be made into two portions which are assembled together to clasp the needle 8 (for example metallic) and the tube 16. Alternatively, the light source 12 and the optical sensor 14 may be made in one-piece. Preferably, the sensor 20 is arranged quite close to the end of the needle 8, at less than 10 cm from the latter, in order to optimise the shear of the red blood cells. Preferably, this distance is about 5 cm to obtain the best results. In one variant, the sensor 20 may be placed directly at the outlet of the needle 8.

Figure 3:
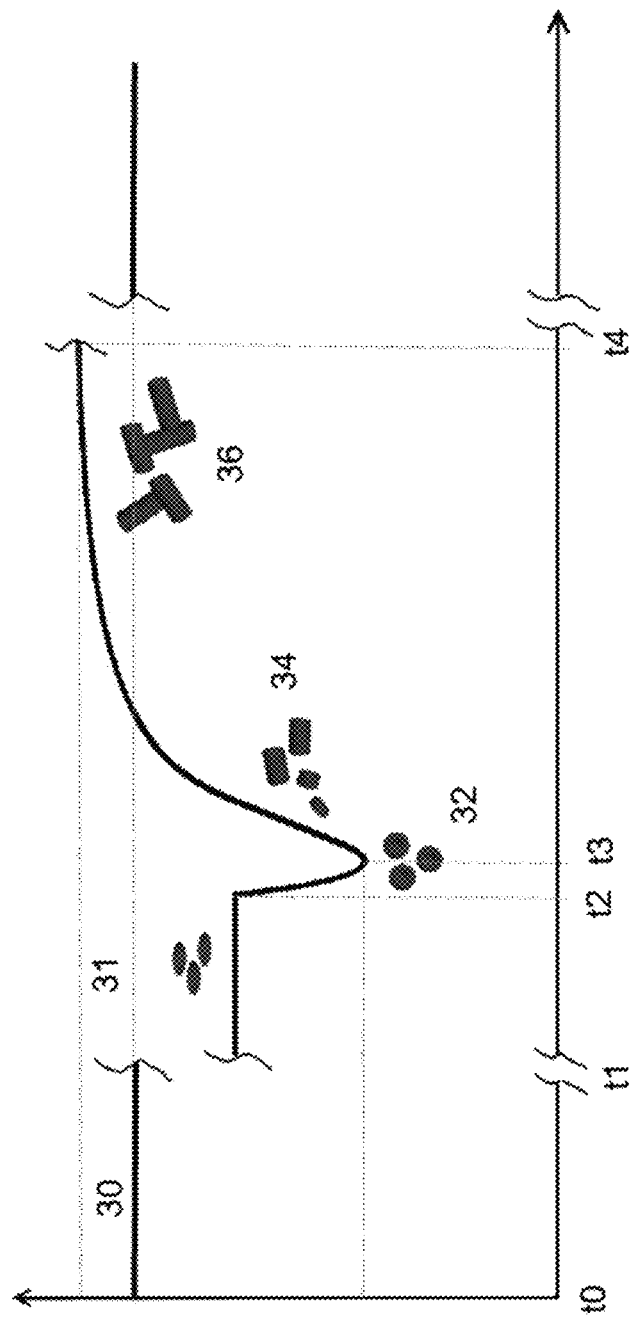
FIG. 3 shows a measurement diagram by the device of FIG. 1.

Irrespective of the configuration, the second group 6 allows advantageously using the diameter of the needle 8 which is conventionally in the range of 1 mm. Indeed, during sampling by the needle 8, the red blood cells undergo successive deformations which are described hereinafter and which are shown in FIG. 3.

Thus, once the needle 8 is immersed into the blood tube 11, the second group 6 controls a suction by the needle 8 already primed with diluent in order to sample blood. This is achieved thanks to automation control means, preparation trays and solenoid valves and syringes that are also known and not shown for simplicity. These means cause movement of the diluent that occupies the tube 16. In this step, because of the translucent nature of the tube 16 and of the diluent contained therein, the sensor 20 measures a constant optical signal.

Afterwards, the blood aliquot is moved up to the sensor 20 by suction. The red blood cells undergo shear, which breaks the aggregation. In this step, the optical signal remains maximum since the blood is not yet opposite the sensor 20. In FIG. 3, this is shown with the reference 30.

When the blood reaches the sensor, the optical signal represents the sheared state of the blood. At this blood shear stage, the haematids have an elongate shape, as shown with the reference 31.

When the suction stops in order to stop shearing, the optical transmission signal drops because the red blood cells recover their biconcave disk relieved form. In FIG. 3, this is shown with the reference 32. Afterwards, the optical signal increases according to a pseudo-logarithmic progression. The progressive increase in the optical signal measured by the optical sensor 14 is related to the progressive aggregation of the free red blood cells. The aggregation is done by stacking red blood cells forming rolls and then three-dimensional structures, which is shown in FIG. 3 with the references 34 and 36.

Beyond about 40s depending on the bloods, the aggregation is substantially slowed down and the sedimentation starts. This start of sedimentation interferes with the measurement of interest which is the aggregation and its correlation with the sedimentation rate. After $t_4$, the blood aliquot is discharged, for example by moving the needle 8 over a tray. Thus, it is proceeded with the discharge of the blood and with rinsing of the tube 16 with diluent, the tube 16 being at the end of this step completely filled with diluent like at the beginning of the procedure described hereinabove.

Four time points are shown in FIG. 3:
- before the time point $t_1$, the tube 16 is filled with diluent,
- the time point $t_1$ marks the time point at which the blood arrives at the level of the sensor 20 by suction,
- the time point t2 marks the time point at which the suction ceases,
- the time point t3 marks the time point beyond which the red blood cells have recovered their relaxed shape, and the aggregation starts,
- the time point t4 marks the procedure end time point, with the discharge of the blood which is again replaced by the diluent, like before the time point $t_1$.

The observation of FIG. 3 shows that the optical signal is less important after the time point t4, while the tube 16 is filled with diluent, than when the tube 16 is filled with blood, which might seem to be paradoxal. This is explained by the fact that, in the example described herein, the optical sensor 14 is conditioned differently before the time point $t_1$ and after the time point t4 of FIG. 3.

Thus, before the time point $t_1$ and after the time point t4, it is determined that the measurement corresponds to a "blank" measurement. Throughout this period, the optical sensor 14 is conditioned by the converter 10 with a minimum measurement gain.

The time point $t_3$ corresponds to the lowest point of the period $t_1$-$t_4$, beyond which the optical signal start increasing, which marks, as described hereinabove, the start of the phenomenon that the invention aims to measure. For this reason, and since the variation of the optical signal remains low between the time point to and the time point $t_1$, in the example described herein, the optical sensor 14 is conditioned with a minimum gain until the time point $t_1$, then with a maximum gain between the time point $t_1$ and $t_4$, and then again with a minimum gain after the time point $t_4$ for the next measurement.

This is even more advantageous as, in the embodiment described herein, the converter 10 is arranged so as to determine a measurement based on the optical density of the signal measured by the optical sensor 14. It should be recalled that the optical density is defined by the formula $DO(t)=\log(KI0/I(t))$ where $I(t)$ is the measurement of the optical sensor at the time point t and K the maxi gain/mini gain ratio. More specifically, the converter 10 is arranged so as to return a sedimentation rate measurement based on the $DO(t_3)/DO(t_4)$ ratio. The Applicant has carried out numerous sedimentation rate measurements using the Westergren reference method which enable the converter 10 to associate the measurements thus calculated with an ESR value.

The Applicant has discovered that it is particularly advantageous to use the optical density, which allows not depending on any variations in the transmittance measurement. The Applicant has also discovered that the converter 10 could also operate based on the ratio $I(t_4)/I(t_3)$, without having to consider the optical density within the Beer-Lambert meaning and using I0 differently in the calculation.

The converter 10 may be made in various manners, for example in the form of an appropriate computer code executed on one or more processor(s). By processors, it should be understood any processor suited to the calculations described hereinbelow. Such a processor may be made in any known manner, in the form of a microprocessor for a personal computer, laptop, tablet or smartphone, an FPGA or SoC type dedicated chip, a computing resource on a grid or in the cloud, a cluster of graphical processors (GPUs), a microcontroller, or any other form capable of providing the computing power necessary to the completion of the process described hereinbelow. One or more of these elements may also be made in the form of specialised electronic circuits such as an ASIC. A combination of a processor and of electronic circuits may also be considered. In the case of the machine learning unit based on gradient boosting, processors dedicated to machine learning could also be considered. Alternatively, the converter 10 may be an analog computer without any programming or computer code as such.

Still alternatively, the converter 10 could use a machine learning algorithm ("machine learning"), which may involve or not a neural network (deep or not). This consists in associating the intensity measurements of the optical sensor 14 with a sedimentation rate value. This variant may be particularly useful to do without the optical density. Still alternatively, the gain of the optical sensor 14 could be the same for all time points of the measurement.

Figure 4:
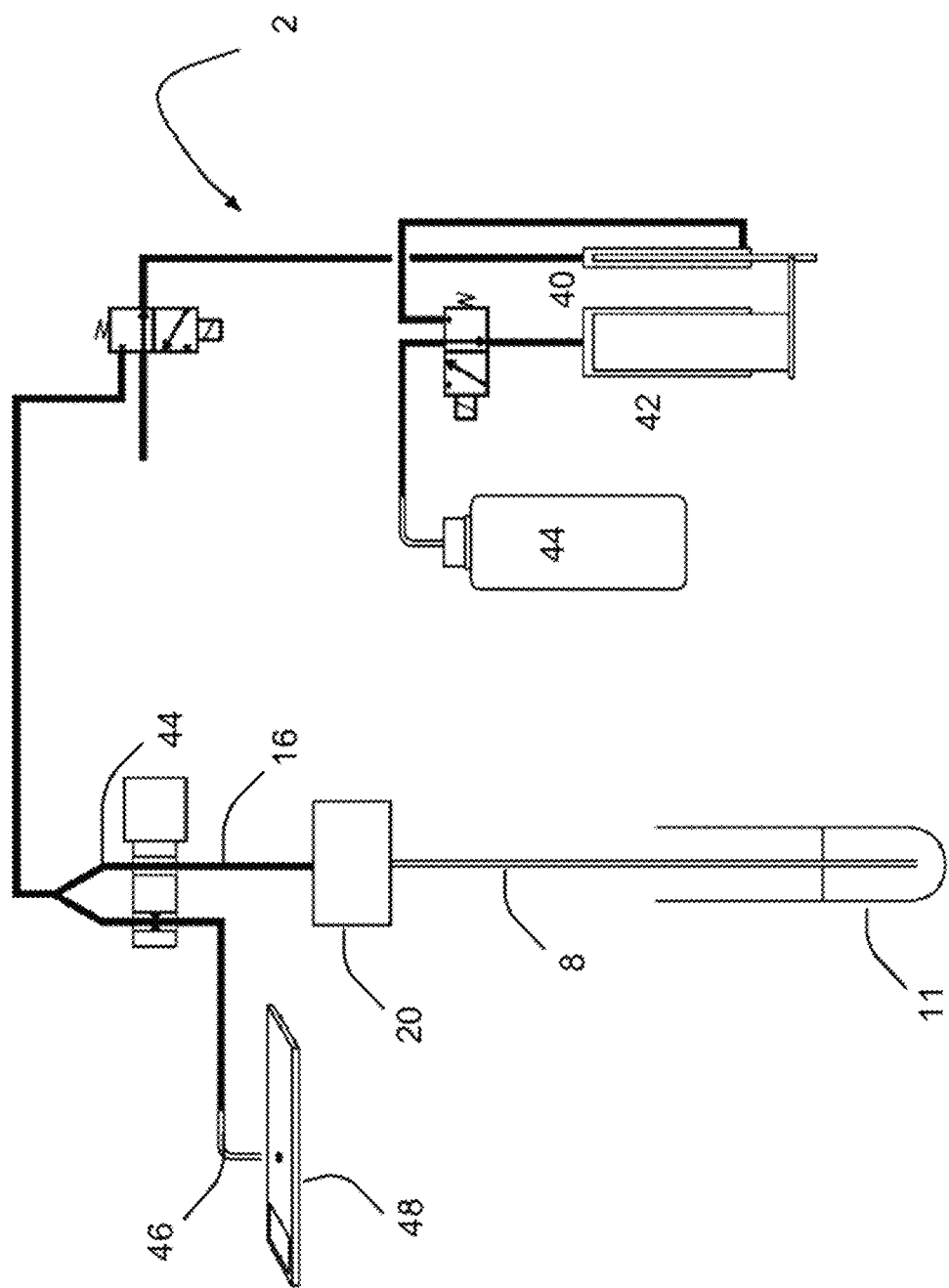
FIG. 4 shows a schematic view of an embodiment of the device of FIG. 1.

FIG. 4 shows a schematic view of an embodiment of the device of FIG. 1. As shown in this figure, the device 2 is a conventional haematology apparatus comprising a syringe 40 with a 1.5 mm diameter, and a syringe 42 with a 16 mm diameter, both of which are connected to the needle 8. The sensor 20 has been integrated on the needle 8, so that it covers the end of the tube 16 connected to the needle 8.

The device 2 of FIG. 4 is adapted to carry out smear test, an ESR measurement or both.

To carry out a smear test by the first group 4, the entire circuit is primed with a diluent, then the needle 8 hits the blood tube 11 and samples about 75 µl with the syringe. During raising thereof, the outside of the needle 8 is progressively rinsed with a flow of liquid pushed on one side and continuously sucked and discharged into the wastes on the other side.

Afterwards, the syringe carries out a removal of the liquid column in order to transfer the aliquot at the Y level of an open pinch valve 44 on the needle 8 side. The pinch valve is activated to close the channel originating from the needle 8 and open the channel towards a drop-off needle 46. Afterwards, the syringe performs a push which allows transferring the sample up to the drop-off needle. A sequence of peripheral rinsing of the drop-off needle and then drying allows ensuring the quality of the aliquot initial front. Finally, a drop of a few microlitres is deposited over a slide 48 by pushing on the syringe.

For the ESR measurement, it is proceeded as described hereinabove with reference to FIGS. 1 to 3. The entire circuit is primed with diluent drawn from a reservoir 44, then an air bubble of a few µL is created at the tip of the needle 8. The needle 8 is lowered into the blood tube 11 and a 50 µL to 100 µL aliquot is sampled by the syringe 42. The needle 8 is raised, and the aliquot transferred to the sensor 20 and the optical measurement of the aggregation is carried out. Finally, the internal and external rinsing of the needle 8 in a tray is carried out, with discharge into the wastes. The blank measurement (I0) may be performed before sampling or at the end of rinsing. The optional comparison of the blank measurements before and after enable an exception handling, for example a control of rinsing.

The smear test and ESR cycles are carried out independently of each other, and involve in particular a separate sampling by the needle 8: the aliquot for the smear test cannot be used for the ESR measurement and vice versa.

This allows decoupling the two operations without any problematic blood sampling when both measurements are requested. This independence makes the measurement ESR much less troublesome for the work rate of the device 2 and enables integration at a lower cost, both with regards to equipment and manpower.

The device of the invention is much more effective than all known systems, which offer either a specific module for measuring the sedimentation rate, in addition to the spreading or colouring module, or to draw off CBC/DIF/RET processing time on a general-purpose module.

Alternatively, the second group 6 may be integrated on the sampling needle of a high-end device which comprises a specific sampling module for subsequent spreading or colouring measurements.

Hence, the invention allows effectively integrating the sedimentation rate measurement to existing devices, without affecting their work rates or their architecture.

The invention claimed is:

1. A device for spreading or colouring and determining a sedimentation rate, comprising a first group arranged so as to sample a blood sample from a tube and to carry out a smear test on the sample,
   a second group arranged so as to sample a blood sample from a tube and to carry out a sedimentation rate determination,
   at least one sampling member which controllable for an operation by the first group and an operation by the second group for sampling a blood sample so that a sample sampled for the first group is not used by the second group, and that a sample sampled for the second group is not used by the first group, the second group being provided with a sensor comprising an infrared light source and an optical sensor arranged substantially opposite one another around a tube connected to an output end of the at least one sampling member so that the light emitted by the infrared light source reaches the optical sensor after having crossed said tube, the second group being further arranged so as to carry out a rinsing of the sampling member and of the tube between two sedimentation rate measurement determinations and the optical sensor being arranged so as to carry out a blank measurement after a rinsing operation, and
   a converter arranged so as to receive a blank measurement and one or more light transmission measurements from the optical sensor and to determine a sedimentation rate from the ratio between the blank measurement and the light transmission measurements.

2. The device according to claim 1, wherein the converter is arranged so as to determine a time point of measurement of the lowest light transmission, and a time point of measurement of the final light transmission.

3. The device according to claim 2, wherein the optical sensor is arranged so as to implement a maximum gain between the time point of measurement of the lowest light transmission and the time point of measurement of the final light transmission, and to implement a minimum gain the rest of the time.

4. The device according to claim 2, wherein the converter is arranged so as to calculate the sedimentation rate from the ratio between (a) the ratio between the blank measurement and the measurement at the time point of measurement of the final light transmission and (b) the ratio between the blank measurement and the measurement at the time point of measurement of the lowest light transmission.

5. The device according to claim 1, wherein the optical sensor is controlled with a low gain before blood passes through the substantially transparent portion, and with a high gain afterwards.

6. The device according to claim 1, wherein the sampling member is a needle which could be controlled for sampling of a blood sample to which a tube is connected in which the substantially transparent portion is formed.

7. A method for spreading or colouring and determining a sedimentation rate comprising using a device according to claim 1, and wherein carrying out a spreading or colouring and determining a sedimentation rate comprise sampling two distinct samples.

8. The method according to claim 7, wherein the converter is arranged so as to determine a time point of measurement of the lowest light transmission, and a time point of measurement of the final light transmission.

9. The method according to claim 8, wherein the optical sensor is arranged so as to implement a maximum gain between the time point of measurement of the lowest light transmission and the time point of measurement of the final light transmission, and to implement a minimum gain the rest of the time.

10. The method according to claim 8, wherein the converter is arranged so as to calculate the sedimentation rate from the ratio between (a) the ratio between the blank measurement and the measurement at the time point of measurement of the final light transmission and (b) the ratio between the blank measurement and the measurement at the time point of measurement of the lowest light transmission.

11. The method according to claim 7, wherein the optical sensor is controlled with a low gain before blood passes through the substantially transparent portion, and with a high gain afterwards.

12. The method according to claim 7, wherein the sampling member is a needle which could be controlled for sampling of a blood sample to which a tube is connected in which the substantially transparent portion is formed.

* * * * *